United States Patent
Ackerman

(10) Patent No.: US 9,241,778 B2
(45) Date of Patent: Jan. 26, 2016

(54) DEVICE AND METHOD FOR CONTROLLING FECAL INCONTINENCE

(75) Inventor: Haim Ackerman, Caesarea (IL)

(73) Assignee: ForConti Medical Ltd., Migdal Haemek (IL)

(*) Notice: Subject to any disclaimer, the term of this patent is extended or adjusted under 35 U.S.C. 154(b) by 565 days.

(21) Appl. No.: 12/987,346

(22) Filed: Jan. 10, 2011

(65) Prior Publication Data

US 2011/0172694 A1      Jul. 14, 2011

Related U.S. Application Data

(60) Provisional application No. 61/293,716, filed on Jan. 11, 2010.

(51) Int. Cl.
*A61F 2/00*      (2006.01)

(52) U.S. Cl.
CPC ............ *A61F 2/0027* (2013.01); *A61F 2/0009* (2013.01); *A61F 2230/0067* (2013.01); *A61F 2230/0069* (2013.01); *A61F 2230/0071* (2013.01); *A61F 2250/0003* (2013.01); *A61F 2250/0059* (2013.01)

(58) Field of Classification Search
CPC ............ A61F 2/0004–2/0027; A61F 5/0093; A61F 5/44
USPC .............. 606/192, 197, 191, 213; 600/29–32; 128/840
See application file for complete search history.

(56) References Cited

U.S. PATENT DOCUMENTS

| | | | |
|---|---|---|---|
| 3,739,750 A * | 6/1973 | Shinjo ........................ 119/174 |
| 4,583,542 A * | 4/1986 | Boyd ........................... 606/197 |
| 4,739,764 A | 4/1988 | Lue et al. |
| 4,813,422 A | 3/1989 | Fisher et al. |
| 5,131,906 A * | 7/1992 | Chen ............................ 600/29 |
| 5,509,427 A * | 4/1996 | Simon et al. ................. 128/885 |
| 6,802,808 B2 | 10/2004 | Brady |
| 6,814,730 B2 | 11/2004 | Li |
| 6,843,766 B1 | 1/2005 | Nemir et al. |
| 6,913,573 B1 | 7/2005 | Viscomi et al. |
| 6,926,701 B2 | 8/2005 | Burns, Jr. et al. |
| 7,318,801 B2 | 1/2008 | Silverman et al. |
| 7,553,273 B2 | 6/2009 | Ferguson et al. |
| 2004/0106943 A1* | 6/2004 | Cappiello et al. ............. 606/192 |
| 2007/0213661 A1 | 9/2007 | Gobel |
| 2008/0281149 A1* | 11/2008 | Sinai et al. ...................... 600/32 |
| 2009/0318750 A1* | 12/2009 | Ziv et al. ......................... 600/29 |

FOREIGN PATENT DOCUMENTS

WO      WO 2007/130953      11/2007

OTHER PUBLICATIONS

European International Search Report completed on May 4, 2011, for European Application No. 11150451.0.

* cited by examiner

*Primary Examiner* — Katherine M Shi
*Assistant Examiner* — Lindsey Bachman
(74) *Attorney, Agent, or Firm* — Pearl Cohen Zedek Latzer Baratz LLP

(57) ABSTRACT

This invention is directed to a device and a method for controlling fecal incontinence. The device of this invention is easily inserted into the anal canal, and is designed for remaining where required in the anal canal or rectum, above the dentate line and hemorrhoidal vein area, despite the peristaltic movements of the intestine.

14 Claims, 4 Drawing Sheets

DEVICE AND METHOD FOR CONTROLLING FECAL INCONTINENCE

CROSS-REFERENCE TO RELATED APPLICATIONS

This application claims priority of U.S. provisional Application No. 61/293,716, filed on Jan. 11, 2010, and entitled "A disposable device for excreta discharge management for patients suffering from fecal incontinence", which is incorporated herein by reference in its entirety.

FIELD OF THE INVENTION

This invention is directed to a device and a method for controlling fecal incontinence. The device of this invention is easily inserted into the anal canal, and is designed for remaining where required in the anal canal or rectum, above the dentate line and hemorrhoidal vein area, despite the peristaltic movements of the intestine.

BACKGROUND OF THE INVENTION

Fecal incontinence is the impaired ability to control bowel movements. Many patients with fecal incontinence have little or no control over their bowel movements, causing distress and embarrassment and limiting the social activity of the patient. In some patients, particularly older ones, fecal incontinence can cause additional problems such as bed sores, which may lead to gangrene, which may, in turn, result in death. Fecal incontinence is a condition that requires substantial time and labor on part of many health care personnel in hospitals and nursing homes, as well as on the part of the family members of the suffering patient.

Several approaches have been used in order to treat, or at least care for, fecal incontinence. The most simple and common method, which does not actually treat the fecal incontinence but which rather treats the consequences thereof, is the use of an absorbent, such as a diaper. However, diapers are not comfortable to wear, cannot be conveniently used in public, and further, may cause bed-sores, mainly in older patients. Other treatments include invasive surgery, which is considered to be a relatively dangerous procedure that cannot be used on all patients, especially if they are suffering from additional conditions or are at an age where invasive surgery may be life threatening.

U.S. Pat. No. 4,813,422 (Fisher et al.) discloses a bowel probe and method for controlling bowel incontinence. The disclosed probe comprises a catheter with an infrared sensor tip, used for sensing fecal mass in the rectum, and a cuff that is inflated to prevent passage of the rectal mass.

However, although previously disclosed devices and methods have, to an extent, been successful in managing incontinence, they are not always reliable or conveniently used. Further, many of the disclosed methods, such as the use of tampon-like devices, create lateral pressure on the rectal wall, which may be both dangerous and painful. Additionally, the anal canal includes two regions, separated by what is known by the dentate line. Generally, the region below the dentate line is highly innervated and, therefore, the presence of a device in that area is painful. The peristaltic movements of the intestines tend to push out anything found within the intestines, and, therefore, they are pushed out of the patient's body, thus being ineffective.

Therefore, there is a need in the art for a non-invasive, reliable device and method for treating fecal incontinence without causing pain or damage to the patient.

SUMMARY OF THE INVENTION

This invention is directed to a fecal incontinence controlling device comprising: a body; a withdrawal means; and a stopper; wherein the body is attached to the withdrawal means and to the stopper, wherein the body comprises an inner surface and an outer surface and blocks fecal matter from moving past it, and wherein the outer surface of the body is configured such that the peristaltic movements cause the body to move upwards in the anal canal or to remain at a required location in the anal canal or rectum and wherein the inner surface is configured so that when the inner surface is exposed, the body moves downwards in the anal canal or rectum.

This invention is further directed to a method for controlling fecal incontinence in a patient comprising: (a) inserting a body of a device into the patient's anal canal, wherein, the body is attached to withdrawal means and to a stopper that remains outside the patient and wherein the body is located above the dentate line in the rectum; (b) optionally filling the body of the device with a gas, a liquid or a combination thereof; and (c) when bowel emptying is desired, withdrawing the device from the anal canal by the withdrawal means; wherein the body comprises an inner surface and an outer surface, wherein the outer surface of the body is such that the peristaltic movements cause the body to move upwards, or remain at a required location in the anal canal or rectum, instead of moving downwards, and wherein the stopper prevents unlimited upward movement of the body of the device.

Additionally, this invention is directed to a method for inhibiting fecal incontinence in a patient comprising: (a) inserting a body of a device into the patient's anal canal, wherein the body is attached to withdrawal means and to a stopper that remains outside the patient, wherein the body is located above the dentate line; (b) optionally filling the body of the device with a gas, a liquid or a combination thereof; and (c) allowing to body of the device to remain in the patient's anal canal and rectum, above the dentate line, until a bowel movement is desired; wherein the body comprises an inner surface and an outer surface, wherein the outer surface of the body is such that the peristaltic movements cause the body to move upwards or to remain at the required location in the anal canal or rectum, instead of moving downwards, and wherein the stopper prevents unlimited upward movement of the body of the device.

BRIEF DESCRIPTION OF THE DRAWINGS

Embodiments of the invention will be understood and appreciated more fully from the following detailed description in conjunction with the figures, which are not to scale, in which like reference numerals indicate corresponding, analogous or similar elements, and in which.

DETAILED DESCRIPTION OF THE PRESENT INVENTION

Figure 1:
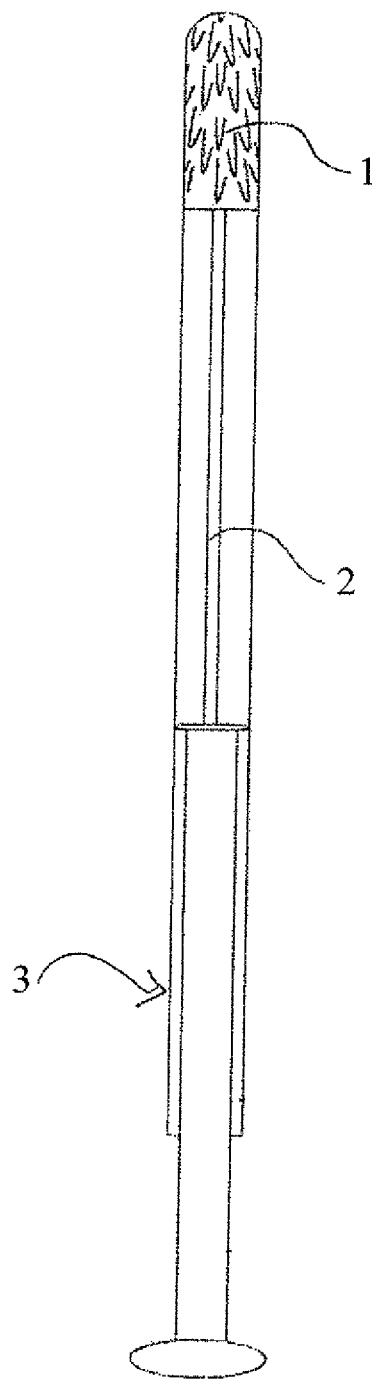
FIG. 1 shows one embodiment of the body of the device in the non-inflated configuration, attached to a syringe.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

This invention provides a fecal incontinence controlling device comprising a body attached to withdrawal means, wherein the body comprises an inner surface and an outer surface, and wherein the outer surface of the body is configured such that the peristaltic movements cause the body to move upwards instead of downwards and to remain at the required location in the anal canal or rectum, and wherein the body is attached to a stopper that prevents unlimited upward movement of the body of the device.

According to one embodiment, the fecal incontinence controlling device of the invention is disposable.

According to this invention, the device blocks fecal matter, thus controlling incontinence, but allows normal blood flow through all of the surrounding tissues. This ensures that no damage, such as necrosis or gangrene, is caused to the patient due to use of the device of the invention.

The body of the device is prepared from any biocompatible synthetic or natural material. According to one embodiment, the body of the device is prepared from silicon or silicon polymers.

According to some embodiments, the body of the device is prepared from biodegradable material. According to this embodiment, the body of the device does not need to be attached to withdrawal means, since, after a certain time, the body of the device biodegrades in the anal canal or rectum and, therefore, does not need to be actively withdrawn therefrom.

According to further embodiments, the body of the device has two configurations: an inflated configuration and a non-inflated configuration. According to one embodiment, the body of the device is inflatable and may be filled with any appropriate liquid or gas, such as water, oil, an iso-osmotic bio-compatible liquid or a lubricant. According to some embodiments, the body of the device is filled using any appropriate means, such as a syringe. According to one embodiment, the body of the device includes a port through which the device is filled. According to further embodiments, the body of the device may be filled at any appropriate location. In an embodiment of the invention, the body of the device is filled so as to substantially seal the anal canal. According to this invention, the contents filling the body of the device remain therein until the body of the device is emptied by the patient or by health aid personnel. According to some embodiments, the body of the device is emptied during the withdrawal thereof from the patient's anal canal.

The body of the device may be of any appropriate shape, size and texture, ensuring that it remains in the anal canal or rectum above the dentate line and hemorrhoidal vein area, at approximately 3-11 cm, e.g., 7 cm, from the anus, blocks the fecal matter from passing it, does not damage the intestine or the anal canal or rectum, and does not cause pain to the patient. For example, the body of the device may be cylindrical, pear shaped, conical or round. According to certain embodiments, the shape of the body of the device changes with pressure, e.g., as a result of the peristaltic movements of the patient's intestine.

According to further embodiments, the body of the device includes an outer surface and an inner surface. The outer surface of the body of the device includes means, such as bristles, jags, notches, indentations, and the like, which on the one hand do not damage the wall of the anal canal or rectum, and on the other hand, cause the peristaltic movements to move the device upwards and further into the intestine, instead of downwards and out of the intestine. According to some embodiments, the inner surface of body of the device is smooth or becomes smooth upon contact with materials such as lubricants.

According to this invention, the body of the device is attached to withdrawal means and to a stopper. According to one embodiment, the body of the device is attached to two separate entities, one acting as a withdrawal means, and the other acting as a stopper. According to another embodiment, the body of the device is attached to a withdrawal means that is attached to a stopper.

When the device is inserted into the anal canal, the stopper remains on the outside of the patient's anus, and prevents the device from moving with no control too high in the intestine. The stopper is prepared from any appropriate material, such as silicon, gum, plastic, or any other biocompatible polymer that eases and prevents irritation.

According to one embodiment, the withdrawal means is a string, a twine or a wire, attached at one side to the top region of the body of the device. According to one embodiment, the withdrawal means is attached also to a stopper.

According to some embodiments, the withdrawal means further comprises a handle, which aids in withdrawing the body of the device from the patient's anal canal, when a bowel movement is desired.

According to one embodiment, the withdrawal means is attached to the top region of the body of the device in such a way that pulling on the withdrawal means causes the body of the device to turn inside-out, exposing the inner surface of the body of the device, which is easily able to move down the anal canal when the device is withdrawn. According to some embodiments, when the body of the device is turned inside-out, the liquid or gas that fills the body is emptied into the anal canal. According to one embodiment, the withdrawal means is attached to the body of the device so that pulling on it causes the inner surface, the outer surface, or both the inner and outer surfaces to tear, thus releasing the liquid or gas within the body of the device into the anal canal or rectum. According to another embodiment, the contents of the body of the device remain therein until the body of the device is removed from the patient's anal canal.

According to further embodiments, the device comprises means for absorbing and/or neutralizing fluids and/or gases, thereby preventing the expulsion of such fluids and gases from the intestine. In an embodiment of the invention, the means comprise active charcoal, botanical extracts and the like. According to certain embodiments, the means for absorbing and/or neutralizing fluids and/or gases are coated on the entire body of the device. According to other embodiments, the means for absorbing and/or neutralizing fluids and/or gases are coated on certain portions of the body of the device. According to some embodiments, the means for absorbing and/or neutralizing fluids and/or gases are incorporated into the body of the device, either partially, or throughout the entire body. According to some embodiments, the anterior part of the body, which is in contact with the fecal material, may be coated or partially coated. According to certain embodiments, the patient is administered medications for preventing and/or reducing gases together with the use of the device of the invention.

This invention further provides a method for controlling fecal incontinence in a patient comprising: (a) inserting a body of a device into the patient's anal canal or rectum through the patient's anus, wherein the body is attached to withdrawal means and to a stopper wherein the stopper remains outside the patient and the withdrawal means is partially within the anal canal and partially outside the patient and wherein the body is positioned at a desired location above the dentate line; (b) optionally filling the body of the device with a gas, a liquid or a combination thereof; (c) allowing to body of the device to remain in the patient's anal canal or rectum, above the dentate line, until a bowel movement is desired; and (d) withdrawing the device from the anal canal by the withdrawal means, allowing the desired bowel movement; wherein the body comprises an inner surface and an outer surface, wherein the outer surface of the body is configured such that the peristaltic movements cause the body to move upwards, or remain at the desired location in the anal canal or rectum, instead of moving downwards, and wherein the stopper prevents unlimited upward movement of the body of the device.

According to this invention, the body of the device may be inserted into the patient's intestine by any appropriate means, such as a designated applicator.

According to one embodiment, the body of the device has two configurations: an inflated configuration and a non-inflated configuration. The body of the device is inserted into the patient's anal canal in the non-inflated configuration, enabling painless and harmless insertion thereof. Once placed above the dentate line and hemorrhoidal vein area, at approximately 3-11 cm, e.g., 7 cm, from the anus, the device is then inflated by filling it with a gas, a liquid or a combination thereof.

This invention further provides a method for controlling fecal incontinence in a patient comprising: (a) inserting a biodegradable body of a device into the patient's anal canal through the patient's anus, wherein the body is attached to a stopper that remains outside the patient and wherein the body is positioned at a desired location above the dentate line; and (b) optionally filling the body of the device with a gas, a liquid or a combination thereof; wherein the body comprises an inner surface and an outer surface, wherein the outer surface of the body is such that the peristaltic movements cause the body to move upwards in the anal canal or to remain at the desired location in the anal canal or rectum, instead of moving downwards, and wherein the stopper prevents unlimited upward movement of the body of the device, and wherein after a certain period of time, the body of the device is biodegraded in the anal canal or rectum.

This invention further provides a method for inhibiting fecal incontinence in a patient comprising: (a) inserting a body of a device into the patient's anal canal or rectum through the patient's anus, wherein the body is attached to withdrawal means and to a stopper that remains outside the patient, wherein the body is positioned at a desired location above the dentate line; (b) optionally filling the body of the device with a gas, a liquid or a combination thereof; and (c) allowing to body of the device to remain in the patient's anal canal or rectum, above the dentate line, until a bowel movement is desired; and wherein the body comprises an inner surface and an outer surface, wherein the outer surface of the body is configured such that the peristaltic movements cause the body to move upwards or to remain at the desired location in the anal canal or rectum, instead of moving downwards, and wherein the stopper prevents unlimited upward movement of the body of the device.

The device may be then withdrawn by the patient or the health care aid or if made by biodegradable material may be degrade so as to allow emptying of the fecal material.

This invention further provides the use of a fecal incontinence controlling device comprising a body attached to withdrawal means, wherein the body comprises an inner surface and an outer surface, and wherein the outer surface of the body is configured such that the peristaltic movements cause the body to move upwards or to remain at the desired location in the anal canal or rectum, instead of moving downwards, and wherein the body is attached to a stopper that prevents unlimited upward movement of the body of the device.

Reference is now made to FIG. 1, which illustrates one embodiment of the invention showing the body 1 of the device in the non-inflated configuration, ready for insertion into the patient's intestine. The body 1 of the device is attached to tube 2, which is attached to syringe 3. Once the body 1 of the device is inserted into the patient's intestine in the non-inflated configuration, and placed therein at a desired location, such as above the dentate line and hemorrhoidal vein area, at approximately 3-11 cm, e.g., 7 cm, from the anus, the body of the device 1 is inflated by filling it with gas and/or liquid that is passed from syringe 3, through tube 2, into the body 1 of the device.

Figure 2:
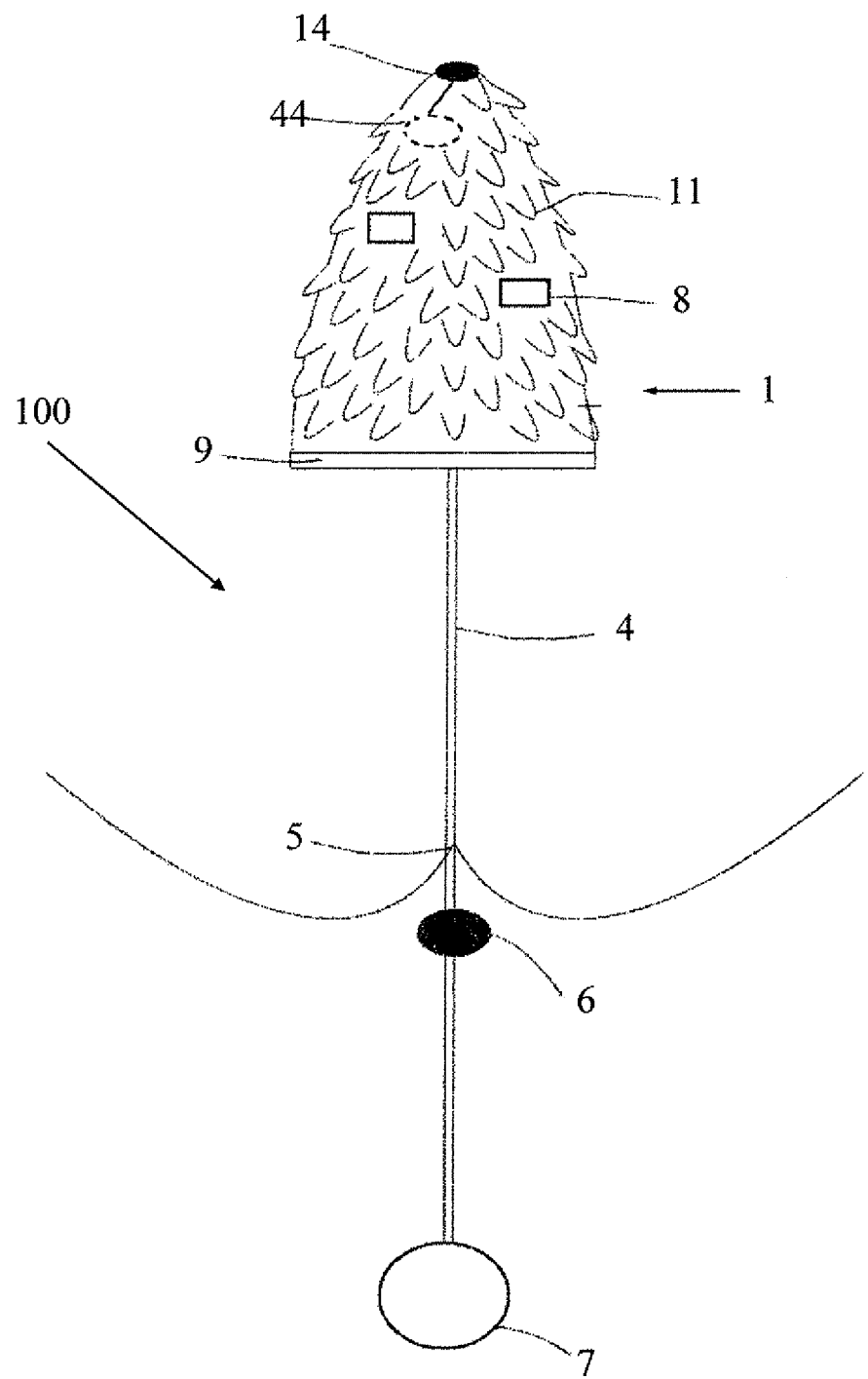
FIG. 2 shows an embodiment of the device with its body in the inflated configuration, as placed in a patient's anal canal.

Reference is now made to FIG. 2, which illustrates the device of the invention 100, wherein the body 1 of the device is in the inflated configuration. The outer surface of the body 1 includes bristles 11, designed so that the peristaltic movements of the patient's intestine cause the body 1 of the device to move upwards in the anal canal or rectum, rather than downwards.

In order to ensure that the body 1 of the device may be removed from the patient's anal canal, and further, that it will not move too far upwards in the intestine while it is situated within the patient's anal canal or rectum, the body 1 of the device is attached to a tether 4, which may be formed of string or twine, which passes through the patient's anus 5. On the outside of anus 5, tether 4 is attached to stopper 6. As described above, the peristaltic movements cause the body 1 of the device to move upwards in the anal canal or rectum. However, stopper 6 is designed so that it cannot pass through anus 5, and, therefore, the upward movement of the body 1 of the device is limited by the length of tether 4, stretching from the body of the device 1 to stopper 6.

In some embodiments, the withdrawal of the body 1 of the device from the intestine is performed by holding onto stopper 6, onto tether 4, or onto both, and pulling away from the patient's body. According to further embodiments, as shown in FIG. 2, a handle 7 is attached to tether 4, aiding in the withdrawal of the body 1 of the device. According to this embodiment, when a bowel movement is desired, the patient or health care aid holds onto handle 7 and pulls downward, thereby withdrawing the body 1 of the device from the patient's anal canal, through anus 5.

As shown in FIG. 2, according to some embodiments, tether 4 may be attached at one or both of two positions on the body 1 of the device, i.e., at tip 14, where the outer surface and the inner surface of the body 1 of the device are connected, and at position 44, which is on the inner surface of the body 1 of the device. In one embodiment, attachment of tether 4 to the body 1 of the device enables the withdrawal of the body 1 of the device without causing pain to the patient or harming the patient, since, when tether 4 is pulled downward, its attachment to tip 14 causes the body 1 of the device to turn inside-out, thus exposing the inner surface of the body 1 of the device, which is designed to move easily down the intestine. In another embodiment, the attachment of tether 4 to position 44 causes the inner surface of the body 1 of the device to tear, thus allowing the gases and liquids within the body 1 of the device to flow out into the patient's anal canal or rectum. According to one embodiment, the emptying of body 1 of the device changes the shape of body 1 so that it easily passes through the anal canal out of anus 5. According to a further embodiment, the gases and/or liquids emptied from body 1 of the device act as lubricants, further aiding in the withdrawal of body 1 of the device from the patient's intestine.

As further illustrated in FIG. 2, the body 1 of the device may be coated with, or include certain regions coated with, or made from, gas absorbing materials 8. The body of the device may further include a strip or several strips 9 for absorbing liquids. According to some embodiments, there may be one material for absorbing both gases and liquids. According to this invention, the gas and liquid absorbing materials may be coated on parts of body 1, coated on the entire outer surface of body 1, be incorporated into certain portions of body 1 or be incorporated into all of the material of body 1. These absorbing materials prevent liquids and gases from leaking past the body 1 of the device and out of anus 5. Absorbing materials 8 and 9 may absorb and/or neutralize any gases or liquids that come into contact with them.

Figure 3:
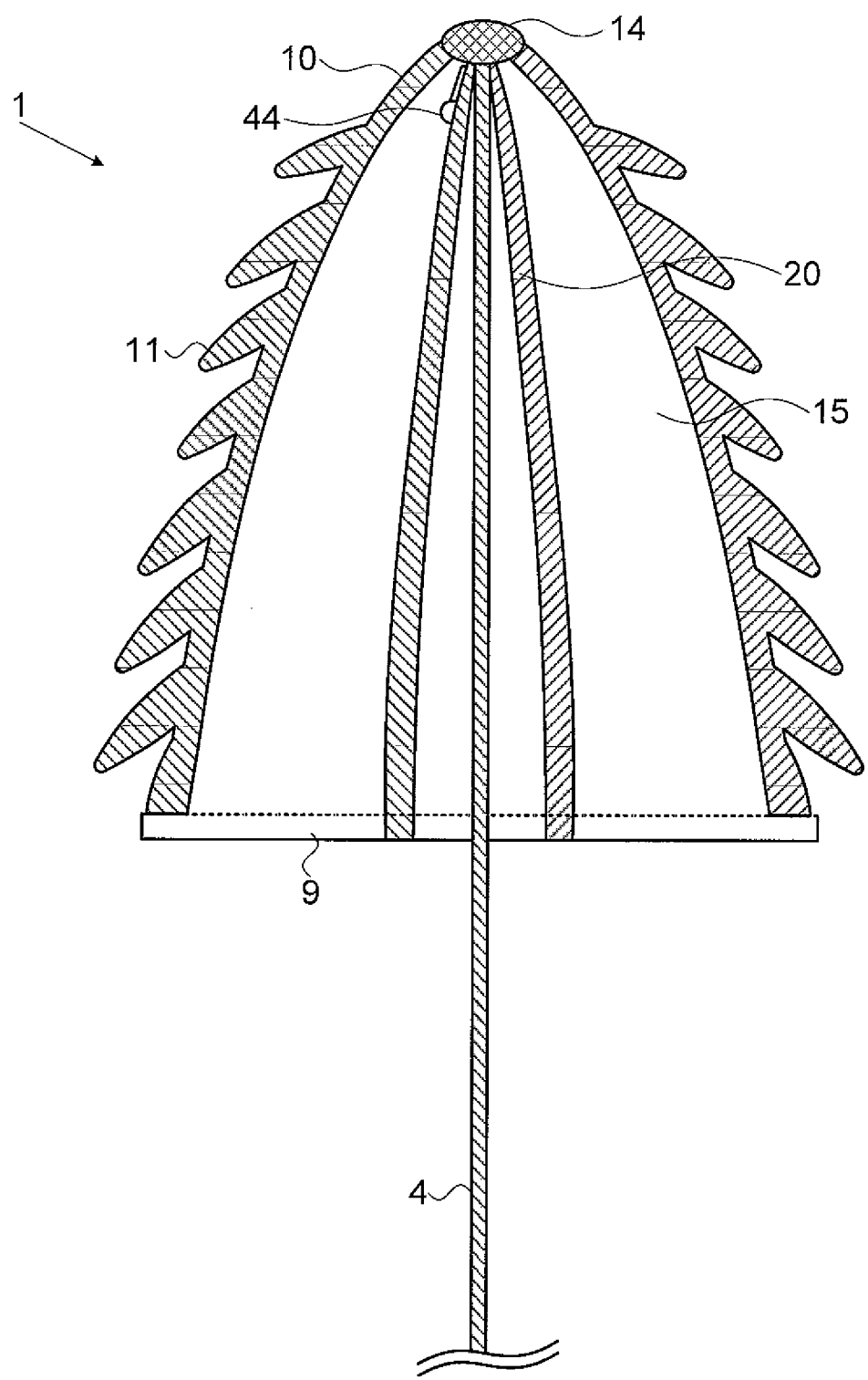
FIG. 3 is a cross sectional view of an embodiment of the body of the device in the inflated configuration.

Reference is now made to FIG. 3, which illustrates a cross section of one embodiment of the inflated configuration of the body 1 of the device. As shown in FIG. 3, the body 1 of the device includes an outer surface 10 and an inner surface 20. The outer surface 10 includes bristles 11, or any other appropriate means, designed so that the peristaltic movements cause the body 1 of the device to move upwards, instead of downwards, in the anal canal. The inner surface 20 on the other hand is designed so as to move freely down the anal canal, without harming or causing pain to the patient. For example, as shown in FIG. 3, inner surface 20 is smooth. In the inflated configuration shown in FIG. 3, area 15, found between outer surface 10 and inner surface 20, is filled with any appropriate gas, liquid, or a combination thereof. In the non-inflated configuration (not shown), area 15 is essentially empty.

As shown in FIG. 3, tether 4 is attached to point 44 on inner surface 20 and to tip 14, where both outer surface 10 and inner surface 20 are connected. Tether 4 can be any appropriate withdrawal means, such as string, twine or wire. When tether 4 is pulled downwards, inner surface 20 is torn at point 44, thus emptying area 15 of the gases and/or liquids found therein. According to one embodiment, the emptying of gases and/or liquids from within area 15 of the body 1 of the device into the anal cavity provides lubrication for the device to ease its withdrawal from the patient. According to another embodiment, the emptying of gases and/or liquids from within area 15 of the body 1 of the device into the anal cavity changes the shape of body 1, so as to ease the withdrawal thereof from the patient's intestine. Further, in light of the attachment of tether 4 to tip 14, the body 1 of the device is turned inside-out, thus exposing smooth inner surface 20, while covering outer surface 10, so that the body of the device 1 moves easily outward when withdrawn from the patient's anal canal.

Figure 4:
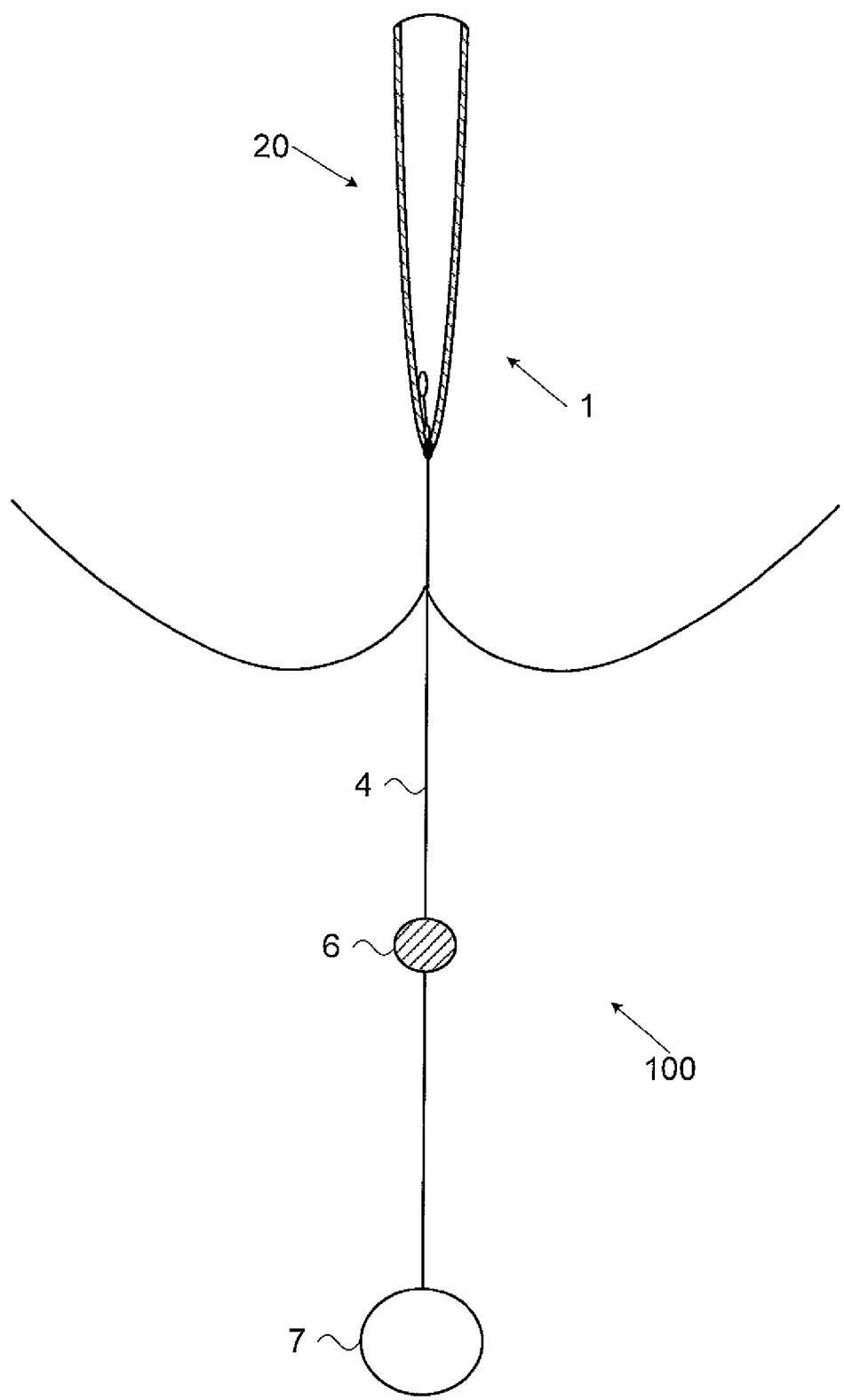
FIG. 4 shows one embodiment of the device of the invention, while being withdrawn from a patient's anal canal or rectum.

Reference is now made to FIG. 4, which illustrates the device 100 in the process of being withdrawn from the patient's anal canal. As shown in FIG. 4 and as detailed above, during withdrawal, the body 1 of the device turns inside-out, exposing the smooth inner surface 20, which easily moves down the intestine, aided both by peristalsis and by the patient or health care aid, who holds onto handle 7 and pulls away from the patient's body. As shown in FIG. 4, when being withdrawn, the body of the device 1 is in the non-inflated configuration. Movement of the device body 1 of the device out of the anal canal may also be aided by the lubrication caused by the presence of gases and/or liquids that were emptied into the anal cavity from within area 15 of the body 1 of the device and by the change of the shape of body 1 when area 15 is emptied.

Although, according to the description above, the device of the invention is placed in the patient's anal canal or rectum, it should be understood that this invention includes the placement of the device in any necessary point in the patient's intestine that is above the dentate line and Hemorrhoidal Vein area, even beyond the anal canal. The device then remains in the required location in the patient's intestine until a bowel movement is desired, or until is biodegrades, in the embodiment where the body of the device is prepared from biodegradable materials.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A fecal incontinence controlling device comprising:
a body;
a withdrawing device comprising a tether; and
a stopper;
wherein the body is attached to the withdrawing device and to the stopper by said tether,
wherein the body has an inflated and a non-inflated configuration and comprises an inner surface and an outer surface and blocks fecal matter from moving past it when in an inflated configuration,
wherein the outer surface of the body comprises bristles, jags, notches, indentation or any combination thereof and is configured such that the peristaltic movements cause the body to move upwards in the anal canal or to remain at a required location in the anal canal or rectum and wherein the inner surface is smooth and is configured so that when the inner surface is exposed, the body moves downwards in the anal canal;
wherein the outer surface and the inner surface are connected at a position on the body of the device;
wherein said tether is attached to two points on the body, one point causing the body to turn inside out, thereby exposing the inner surface, and the other point causing the inner surface, the outer surface, or both the inner surface and the outer surface to tear when the withdrawing device is used to withdraw the body from a patient's anal canal; and
wherein said stopper is an external stopper attached to said body of said device by said tether, which is long enough, such that when the body of the device is placed above the dentate line, the stopper remains outside the body of the patient.

2. The fecal incontinence controlling device according to claim 1, wherein, in the inflated configuration, the body is filled with water, oil, a lubricant or an iso-osmotic biocompatible liquid.

3. The fecal incontinence controlling device according to claim 1, wherein the body is prepared from silicon.

4. The fecal incontinence controlling device according to claim 1, wherein the body is of any shape that blocks fecal matter from moving past the body, when positioned in a patient's anal canal or rectum, while not damaging the anal canal or rectum or causing pain to the patient.

5. The fecal incontinence controlling device according to claim 4, wherein the shape of the body changes with pressure.

6. The fecal incontinence controlling device according to claim 1, wherein the tether is a string, twine or wire.

7. The fecal incontinence controlling device according to claim 1, wherein the withdrawing device comprises a handle.

8. The fecal incontinence controlling device according to claim 1, further comprising materials for absorbing or neutralizing fluids, gases, or a combination thereof.

9. The fecal incontinence controlling device according to claim 1, wherein the body is attached to the withdrawing device that is attached to the stopper.

10. The fecal incontinence controlling device according to claim 1, wherein the device is disposable.

11. The fecal incontinence controlling device according to claim 1, wherein the outer surface and inner surface are connected at a tip of the body of the device.

12. The fecal incontinence controlling device according to claim 1, wherein the tether is attached to a tip of the body of the device.

13. The fecal incontinence controlling device according to claim 12, wherein the tether is further attached to a point on the inner surface.

14. The fecal incontinence controlling device according to claim 1, wherein the tether is attached to the position on the body of the device where the inner and the outer surface are connected.

\* \* \* \* \*